United States Patent [19]

Myers

[11] Patent Number: 5,836,977
[45] Date of Patent: Nov. 17, 1998

[54] DEFIBRILLATOR METHOD AND SYSTEM FOR MAKING POST-DISCHARGE MEASUREMENTS OF ENERGY AND IMPEDANCE

[75] Inventor: Richard C. Myers, McMinnville, Oreg.

[73] Assignee: Hewlett-Packard Company, Palo Alto, Calif.

[21] Appl. No.: 967,271

[22] Filed: Nov. 7, 1997

Related U.S. Application Data

[63] Continuation of Ser. No. 741,894, Oct. 31, 1996, abandoned.

[51] Int. Cl.$^6$ ........................................................ A61N 1/39
[52] U.S. Cl. ........................................................ 607/5; 607/8
[58] Field of Search ............................................... 607/5, 8

Primary Examiner—William E. Kamm
Assistant Examiner—George R. Evanisko

[57] ABSTRACT

A defibrillator incorporates a method and device for determining the energy delivered to and electrical resistance of biological tissues. The defibrillator's method and device achieve these determinations by measuring the pre-discharge voltage on the defibrillator's capacitors which are to be discharged into the body; measuring the post-discharge voltage across the capacitors which are subsequently discharged into the biological tissues; and calculating both the energy delivered to the biological tissues and the electrical resistance of the biological tissues on the basis of the measured pre-discharge and post-discharge defibrillator capacitor voltages.

4 Claims, 3 Drawing Sheets

DEFIBRILLATOR METHOD AND SYSTEM FOR MAKING POST-DISCHARGE MEASUREMENTS OF ENERGY AND IMPEDANCE

CROSS REFERENCE TO RELATED APPLICATION

This is a continuation of application Ser. No. 08/741,894 filed on Oct. 31, 1996, now abandoned.

BACKGROUND

1. Technical Field

The present invention relates, in general, to an improved defibrillator. In particular, the present invention relates to an improved defibrillator having the ability to sense the electrical resistance between electrodes connected to biological tissues and to be able to determine the quantity of electrical energy discharged by a defibrillator capacitor through the electrodes and into the biological tissues. Still more particularly, the present invention relates to an improved defibrillator having the ability to sense the electrical resistance between electrodes connected to biological tissues and to be able to determine the quantity of electrical energy discharged by a defibrillator capacitor through the electrodes and into the biological tissues by using the pre-discharge and post-discharge measured voltages on the defibrillator capacitor which has been discharged.

2. Description of Related Art

The heart is generally described as being composed of four chambers: the right atrium, the right ventricle, the left atrium, and the left ventricle. There is a one-way valve between the right atrium and the right ventricle (the tricuspid valve). There is a one-way valve between the right ventricle and the arterial system which perfuses the lungs (the pulmonic valve). There is a one-way valve between the left atrium and the left ventricle (the mitral valve). And, lastly, there is a one-way valve between the left ventricle and the aorta (the aortic valve).

In terms of its functional operation, the heart receives oxygen-depleted blood via the vena cavae (the two large veins which return blood to the heart). These large veins empty into the right atrium. The right atrium then pushes this oxygen-depleted blood into the right ventricle. Next, the right ventricle pushes this oxygen-depleted blood into one long, continuous fluid path composed of, in sequence, the pulmonary artery, the capillary beds perfusing the lungs, and the pulmonary veins which empty into the left atrium. The continuous path ends with the left atrium, which is to say that there is no valve between the pulmonary veins and left atrium. Next, the oxygen rich blood which has entered the left atrium is pushed into the left ventricle. Finally, the left ventricle pushes the blood out into the aorta.

The heart pumps blood by the organized successive contraction of individual heart muscle fibers. A neurological signal spreads through the heart, and each muscle fiber responds by contracting in sequence. The overall effect is a single heartbeat, or heart pulse, moving blood through the heart. For effective pumping, the muscle fibers must contract in an organized fashion.

The neurological signal alluded to in the previous paragraph is effectuated by the spread of an action potential throughout the heart. An action potential is a transient change in cell membrane potential which conveys information, such as the information in a signal telling a heart muscle fiber to contract. When the heart muscle is at rest, the electrical potential on either side of any cell membrane is maintained at a fixed potential. However, when the muscle is stimulated, either electrically, chemically, or mechanically, channels open in the membrane which allow the oppositely charged ions on either side of the membrane to cross the membrane, such ions engaging in an effort to reach electrical and thermal neutrality. This occurrence is referred to as "depolarization," since the system is becoming less polarized as the ions tend toward the lowest energy state. If the stimulation is great enough, the change in potential arising from the ions crossing the membrane will be great enough to depolarize the portion of the membrane directly adjacent to the area of the membrane depolarized by the stimulus. When this occurs, an action potential is said to have been initiated, and the signal will continue to propagate through the fiber via the just-described mechanism of depolarizing that portion of the membrane directly adjacent to the depolarized area. This propagation of the action potential is analogous to the way in which a row of dominoes falls when the first is flicked into the second, and the second falls into the third, and the third falls into the fourth, etc. Once the action potential has propagated past a region of the membrane, the cell membrane resets itself in a process known as "repolarization." In repolarization, ions are actively pumped back across the cell membrane to restore the polarized state.

The functional operation, described above, is effectuated by the electro-chemical and mechanical operation of the heart as follows. The natural pacemaker of the heart, the sinoatrial nerve, discharges an electrochemical pulse, or action potential, and from this action potential all subsequent electrochemical and mechanical activity of the heart ensues. The sinoatrial nerve is located very near the right atrium, so the initial action potential reaches it almost immediately; simultaneously, the action potential propagates along a very fast conduction internodal tract to the left atrium, with the net result being that the atria (plural of atrium) receive the pulse almost simultaneously. Due to the anatomical structure of the heart, the atria initially receive the pulse upstream from the atrioventricular valves which separate the atria from the ventricles. When the pulse is received, the muscle fibers excited first contract first; in practice, what this means is that the atria of the region upstream contract first, so that the blood is pushed in the downstream direction. This operation is greatly analogous to the way in which toothpaste can be most efficiently squeezed out of the tube by squeezing at the closed end of the tube first.

Although, at this point, the atria have received the action potential, the action potential is continuing to propagate throughout the heart. Simultaneous with the just-described actions involving the atria, the action potential is proceeding over three parallel internodal tracts to the atrioventricular node. The atrioventricular node functions as an analog delay; this delay provides time for atrial contraction to occur (the atria contract with more force over time as more fibers are recruited into contraction), which will enhance the functioning of the atria. After the delayed action potential leaves the atrioventricular nerve, it is conducted along a neural structure known as the bundle of His. Subsequent to this, the neural structure splits and the action potential is conducted by the right and left bundle branches to the regions of the right and left ventricles. Once the action potential arrives at the regions of the right and left ventricles, the action potential activates the Purkinje fibers, which are very fast conduction fibers that conduct the action potential very rapidly over and throughout the ventricles.

Once the ventricles are energized (depolarized), they begin to contract. The ventricles are much stronger and contract more rapidly than the atria (which are, at this point, continuing to contract). Very quickly, the pressure in the ventricular chambers outstrips that of the atria, causing both the mitral and the tricuspid valves to slam shut (because the pressure on the upstream side of these one-way valves exceeds the pressure on the downstream side). Once the right ventricle has outstripped the pressure of the contracting left atrium, the pulmonary valve opens and blood is pumped into the fluid path consisting of the pulmonary artery, capillary bed, pulmonary vein, and left atrium. Subsequent to this, once the left ventricle has outstripped the pressure of the aorta, the aortic valve opens and blood is pushed into the aorta. Once the ventricles have ejected the majority of their contents, the ventricles begin to relax and both the pulmonic and aortic valves close, with the pulmonic valve generally closing first due to the proximity of the continuing-to-contract left atrium.

Once the pressure in the relaxing ventricles falls below that of the continuing-to-contract atria, the atrioventricular valves (tricuspid and mitral) open and the atria push blood into the ventricles. Once the atria have completed this task, they relax and the heart enters a wait state after which the whole foregoing-described process is re-initiated by the next sinoatrial pulse.

As has been alluded to above, it is very important that the action potential proceed as an orderly wave throughout the heart so that the heart muscles squeeze the blood through the lungs and out of the heart through the aorta and the rest of the body. That is, even the very rapid Purkinje fibers conduct the signal from first stimulated to last stimulated, which ensures the correct direction of "push." Returning to our toothpaste analogy, the orderly conduction of the wave assures that the tube will be squeezed from the correct end.

Imagine what would happen, then, if the beautifully synchronized action potential wave became disrupted. In fact, specifically imagine what would happen if the wave through the Purkinje fibers became unsynchronized such that a region of the fibers that was to be depolarized subsequent in time to another region further upstream spontaneously depolarized either before, or simultaneous with, the region that should have depolarized first. Note that the effect of this spontaneous depolarization would be the heart working against itself, in that if the regions simultaneously depolarized the blood would be simultaneously pushed forwards (upstream) and backwards (downstream) and would go nowhere; furthermore, if the regions sequentially depolarized but in the wrong order, the blood would be first pushed backwards and then forwards with the net result being that the blood would go nowhere. When this phenomenon occurs on a large scale, the result is termed "fibrillation."

A fibril is one of the fine threads into which a striated muscle can be longitudinally split. "Fibrillation" is a term coined in the mid-to-late 1800s and refers to the preceding-described unsynchronization to the point such that it appears each muscle fiber of the heart is contracting randomly and independent of the other fibers. Since the muscle fibers where the spontaneous action potentials occur contract, and since this contraction is not in any way synchronized with the other action potentials, the result is chaotic, with the result being that no blood is pumped out of the heart because the different parts of the heart muscle are not acting in synchrony. In fact, a heart in fibrillation is often described as resembling a quivering bag filled with worms, since the asynchronous contractions of different bands or fibers of muscle resembles the surface of a bag filled with writhing worms.

"Defibrillation" is the causing of the cessation of the chaotic and uncoordinated contraction of the ventricular myocardium arising from the spontaneously occurring action potentials by the application of an electrical voltage and current. Defibrillation is achieved when the electrical energy supplied is large enough to depolarize a major portion of the heart muscle such that virtually the entire heart muscle is simultaneously depolarized. Once this is done, all portions of the heart muscle repolarize virtually simultaneously and the heart is in its resting state. An analogous way to think of defibrillation is the resetting of the heart to its wait state. Then, once the sinoatrial nerve fires, the heart muscle propagates the action potential in the correct synchronous fashion, since the defibrillation put all portions of the heart back in synch.

In practice, the application of the electrical voltage and current to the fibrillating heart is achieved via the discharge of one or more capacitors into the fibrillating heart muscle. A capacitor, also known as an electrical condenser, is a device for storing potential energy in the form of electrical charge. In its simplest form a capacitor consists of two metal plates separated by a nonconducting layer called the dielectric. When one plate is charged with electricity from a direct-current or electrostatic source, the other plate will have induced in it a charge of the opposite sign; that is, positive if the original charge is negative and negative if the charge is positive.

The electrical size of a capacitor is its capacitance, the amount of electric charge it can hold. Since the normal state of nature is to be in electrical neutrality, if the negative and positive plates of the capacitor are connected via a conductor, the electrons will seek to redistribute themselves such that electrical neutrality is reached; in other words, the electrons will give rise to the flow of an electric current. When the electrons flow toward the lowest energy state (electrical neutrality), that flow can be used to produce useful work (much in the same way that a waterfall can turn a waterwheel). And in the case of defibrillator, that useful work is the cessation of a heart in fibrillation. The way this is done is that one or more pairs of electrodes are placed proximate to the heart, and from those pairs of electrodes electrical conductors are connected via electrical switching to one or more charged capacitors. The electrodes are of a type to allow the electrical energy of the capacitors to discharge into the biological tissues.

In practice, it is sometimes difficult to electrically energize the heart such that the desired uniform depolarization occurs; furthermore, the stimulating signal must be of a type to avoid the possibility of itself reinducing fibrillation once it is terminated. Toward this end, physiologists have tried using various different stimulating waveforms in conjunction with various different numbers of stimulating defibrillation electrodes.

Experimentation has shown that there are optimal energy levels which can be delivered by defibrillators in conjunction with varying numbers of electrodes which are most likely to defibrillate the heart and avoid the likelihood of reinducing fibrillation; furthermore, experimentation has also shown that there are optimum patterns of energy delivery. In order to adequately assess whether the optimum energy levels are being delivered, precise knowledge of the energy discharged by the capacitors needs to be known. And in order to ensure that the optimum patterns of discharge are being used, it is essential that the electrical resistance of the biological tissues between any electrodes through which the capacitor is discharging be known.

The need for knowledge of both the energy delivered and the electrical resistance is known and determined in the prior art. In the prior art the electrical resistance of the biological tissues between electrodes is derived as follows. First, the initial voltage on any capacitor of interest is determined. Second, after a closed circuit has been formed between the discharge capacitor and the biological tissues, a current measuring circuit is used to determine the initial surge current that occurred when the capacitor was initially connected through the biological tissues. Third, the initial surge current and initial voltage of the capacitor are used to determine the electrical resistance initially offered by the biological tissue between the two electrodes.

In the prior art, the energy delivered to the biological tissue is calculated as follows. Circuitry is used to record the duration of time during which the capacitor was connected to biological tissues. Once the capacitor has been disconnected from the biological tissues, it is assumed that the biological tissues were purely resistive. On the basis of this assumption the exponential decay formula for a resistive-capacitive ("RC") circuit is used to calculate the final voltage on the capacitor by using the recorded time of discharge and calculated resistance. On the basis of this, the energy equation of a capacitor, $CV^2/2$, is used to calculate both the initial and final energy stored within the capacitor, with the difference between the two being deemed the energy delivered.

The discussed defibrillators are often implanted, meaning they are contained within the body of the person whose heart is being defibrillated. Accordingly, both the power requirements and space requirements of defibrillator requirements are crucial; the power requirements are crucial because the implanted defibrillators often use batteries, so the smaller the drain on the batteries the better, and the space requirements are important because most of the space inside the human body has already been taken up by biological organs. Thus, a need exists for defibrillators which will perform the functions necessary for precise defibrillation with as few electronic components as possible, since each additional electronic component consumes additional battery power and takes up space.

The present invention meets this need by providing all information (namely, the electrical resistance of the biological tissues and a measure of the energy delivered to the biological tissues during discharge) as that provided in the prior art, but doing so in such a fashion that the circuitry necessary to measure the initial surge current is no longer needed. The present invention accomplishes this by utilizing previously unutilized information—the measured final voltage on the discharge capacitor—to calculated both the electrical resistance and the energy discharged.

SUMMARY OF THE INVENTION

It is therefore one object of the present invention to provide an improved defibrillator.

It is another object of the present invention to provide an improved defibrillator having the ability to sense the electrical resistance between electrodes connected to biological tissues and to be able to determine the quantity of electrical energy discharged by a defibrillator capacitor through the electrodes and into the biological tissues.

It is yet another object of the present invention to provide an improved defibrillator having the ability to sense the electrical resistance between electrodes connected to biological tissues and to be able to determine the quantity of electrical energy discharged by a defibrillator capacitor through the electrodes and into the biological tissues by using the pre-discharge and post-discharge measured voltages on a defibrillator capacitor which has been discharged.

The foregoing objects are achieved as is now described. A defibrillator incorporating a method and device are provided for determining the energy delivered to and electrical resistance of biological tissues. The defibrillator's method and device achieve these determinations by (1) measuring the pre-discharge voltage on the defibrillator's capacitors which are to be discharged into the body; (2) measuring the post-discharge voltage across the capacitors which are subsequently discharged into the biological tissues; and (3) calculating both the energy delivered to the biological tissues and the electrical resistance of the biological tissues on the basis of the measured pre-discharge and post-discharge defibrillator capacitor voltages.

The above as well as additional objects, features, and advantages of the present invention will become apparent in the following detailed written description.

BRIEF DESCRIPTION OF THE DRAWINGS

The novel features believed characteristic of the invention are set forth in the appended claims. The invention itself, however, as well as a preferred mode of use, further objects, and advantages thereof, will best be understood by reference to the following detailed description of an illustrative embodiment when read in conjunction with the accompanying drawings, wherein:

DETAILED DESCRIPTION OF PREFERRED EMBODIMENT

Figure 1:
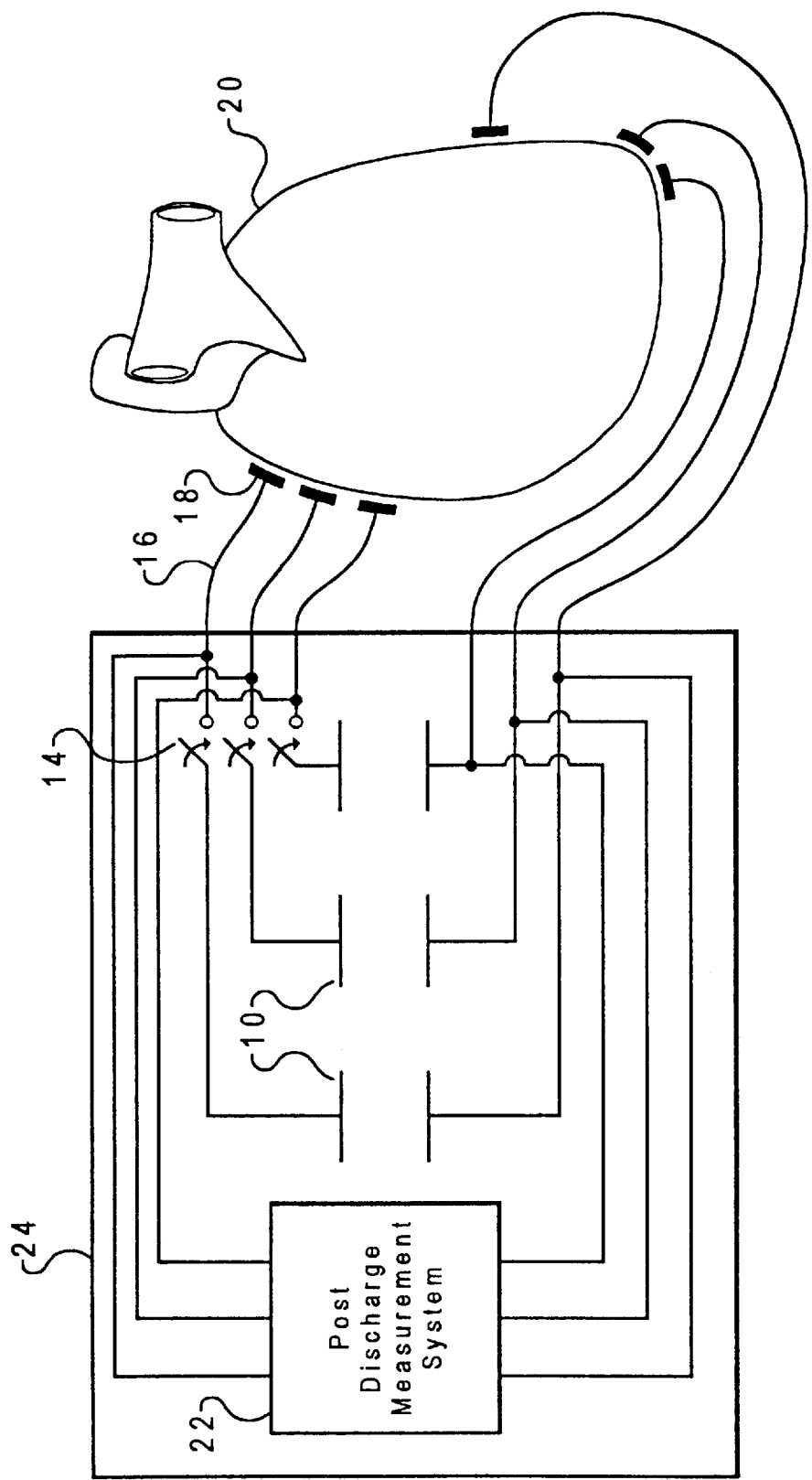
FIG. 1 illustrates a high-level schematic view of a system for implementing the present invention.

With reference now to the figures and in particular with reference to FIG. 1, there is depicted a high-level schematic view of a system for implementing the present invention. FIG. 1 depicts a heart and surrounding biological media, which will be referred to as "biological tissues" 20 to which two or more defibrillation electrodes 18 are proximate. The electrodes are connected via the conducting cables 16 to the defibrillator 24. Within the defibrillator 24 at least one of the defibrillation electrodes 18 is connected to either end of one or more discharge capacitors 10 through switching devices 14. Connected in parallel with each of the one or more capacitors to be discharge is the Post-Discharge Measurement System 22. It will be understood by those in the art that each capacitor shown in FIG. 1 could be composed of multiple capacitive elements.

Figure 2:
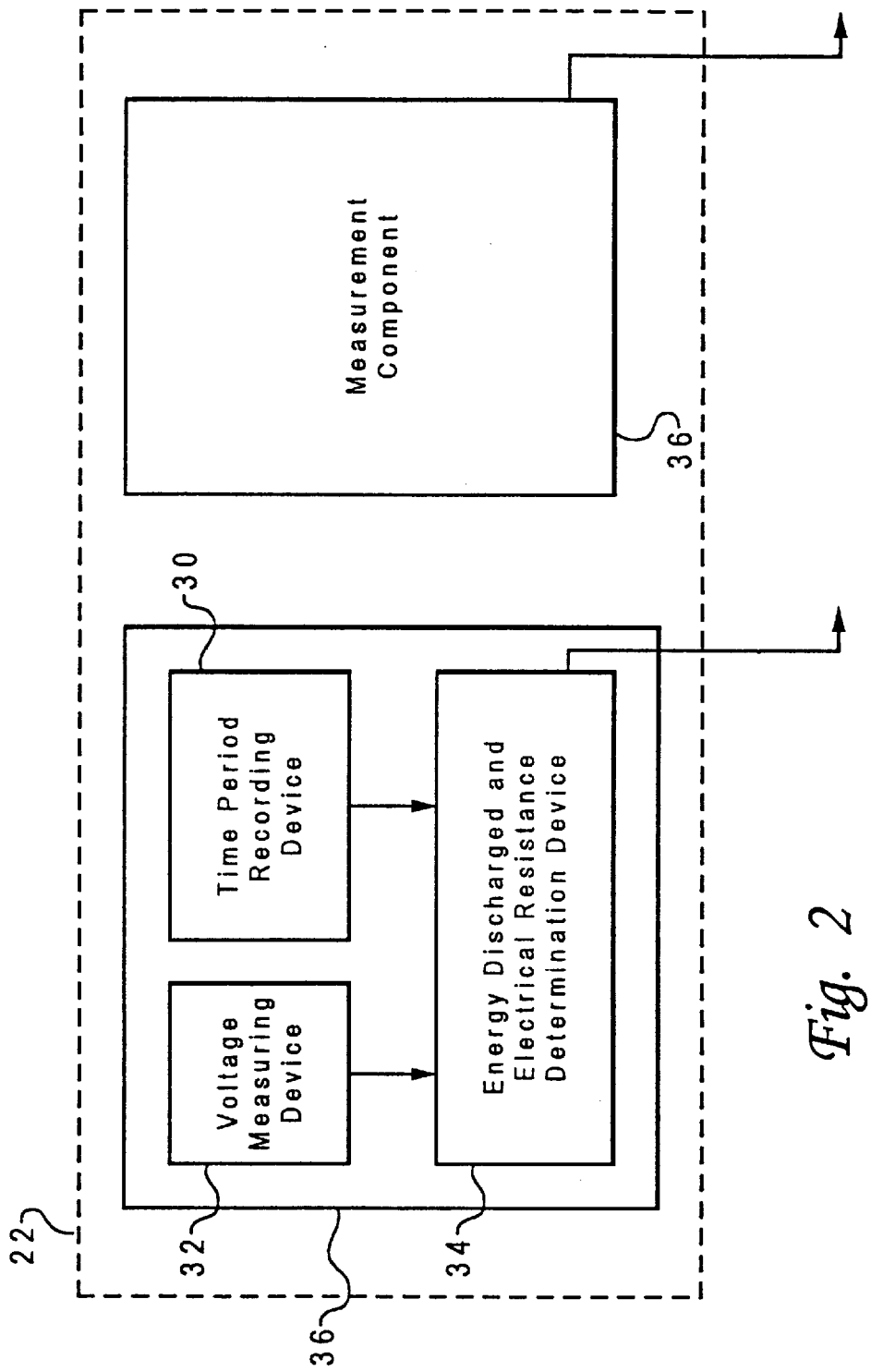
FIG. 2 is a schematic diagram illustrating a first embodiment of the Post-Discharge Measurement System 18 shown in FIG. 1.

FIG. 2, shows a schematic diagram illustrating a first embodiment of the Post-Discharge Measurement System 22. Only one Measurement Component 36 is shown in detail in FIG. 2, but it will be appreciated by one skilled in the art that the Post-Discharge Measurement System 22 will be composed of any number of Measurement Components 36 necessary to accommodate the number of capacitors actually used in defibrillator 24. Each Measurement Component 36 receives a signal from a switching device 14 indicating that the discharge capacitor 10 associated with the device is in the process of being connected to the load, and based on this signal the Voltage Measurement Device 32 records the pre-discharge initial voltage on the capacitor and the initialization of the Time of Discharge Recording Device 30. Upon disconnection of the discharge capacitor 10 from the load (composed of both the conducting cables 16, the defibrillation electrodes 18, and the biological tissues 20 between the defibrillation electrodes 18) the switching device 14 notifies the Measurement Component 36 of this fact, prompting the Voltage Measurement Device 32 to record the post-discharge voltage on the capacitor and the termination of the interval recorded by the Time of Discharge Recording Device 30.

At the termination of the discharge interval, the Voltage Measurement Device 32 delivers the pre-discharge initial voltage and the post-discharge initial voltage to the Energy Discharged and Resistance Determination Device 34; contemporaneous with this, the Time of Discharge Recording Device 30 delivers the recorded interval of discharge to the Energy Discharged and Resistance Determination Device 34. The Energy Discharged and Resistance Determination Device 34, which could be a microcomputer, recalls a circuit model which is then used in conjunction with the pre- and post-discharge voltages and recorded interval of discharge (exact details of how this information is used is described in connection with FIG. 3, below) to determine a measurement of the electrical resistance offered to the capacitor, which is deemed the electrical resistance offered by the biological tissues 20, and to determine the energy discharged by the discharge capacitor 10, which is deemed to be the energy discharged into the biological tissues 20. As is discussed below with respect to method step 50 of FIG. 2, the most accurate resistance calculations will be those obtained when a single capacitor discharges through a single path. This information is then output as a signal on output line 38, which is then routed to the appropriate control device (not shown).

It is reiterated here that the preferred embodiment will have a measurement component for each discharge capacitor 10 of interest.

Figure 3:
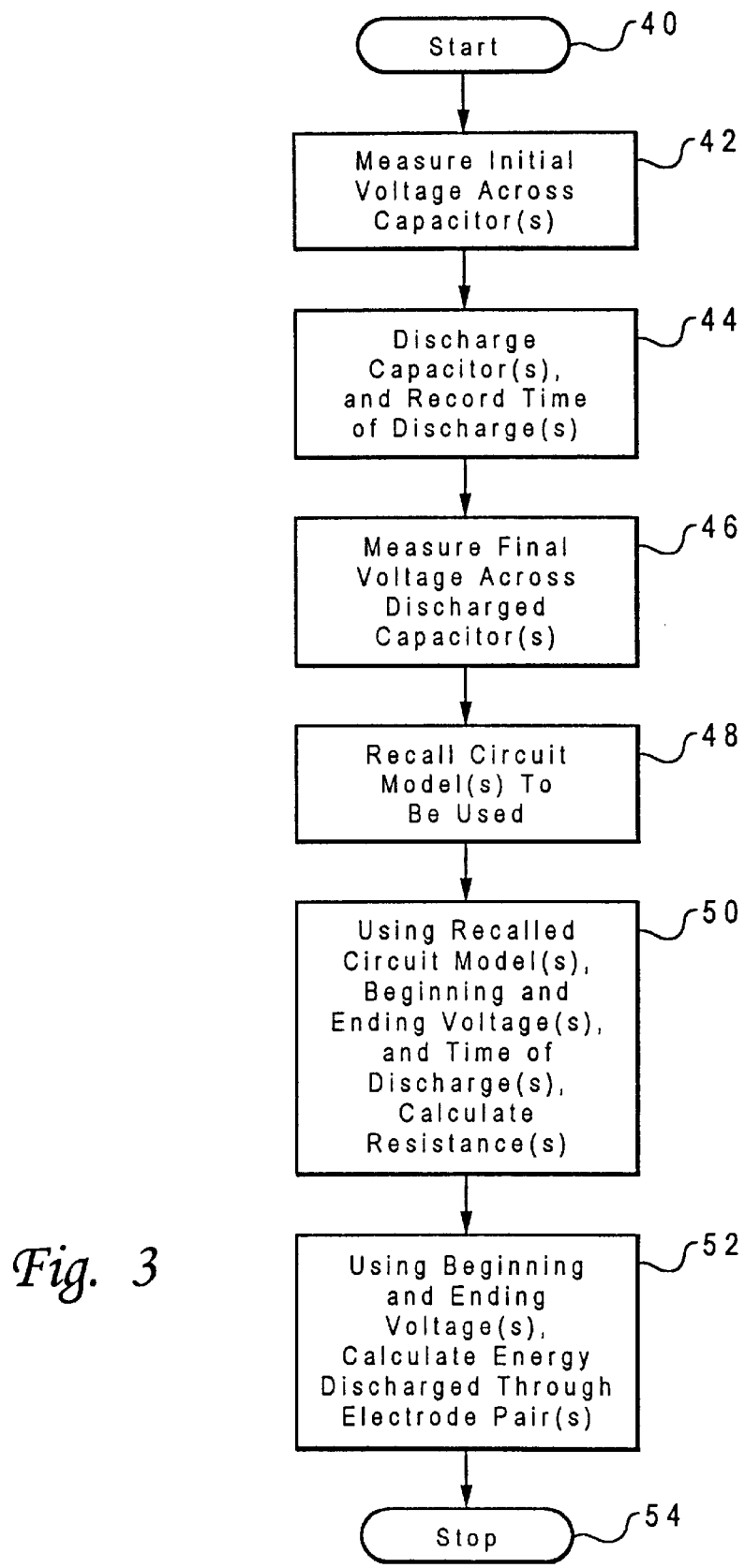
FIG. 3 is a high-level logic flowchart depicting the process whereby the present invention determines the post-discharge measurements.

FIG. 3 shows a high-level logic flowchart depicting the process whereby the present invention determines the post-discharge measurements. Step 40 shows the beginning of the process. Step 42 illustrates the measuring of the pre-discharge voltage on the capacitor to be discharged into biological tissues 20.

Step 44 shows the subsequent method step of discharging the capacitor into the biological tissues 20 and the recording of the time period during which the capacitor was discharging. Next, Step 46 depicts the measuring of the final voltage on the capacitor that was discharged into the biological tissues 20. Method Step 48 shows the recall of a circuit model, which will be used to approximate the capacitor-biological tissues electric circuit, as an electric circuit made up of elements which can be treated and solved by engineering circuit theory models; specifically, in one embodiment of the present invention, the circuit model recalled is that of a capacitor discharged into a purely resistive circuit element, whose solution has the form $V_f = V_i e^{-t/RC}$, where t is the amount of time the capacitor is kept connected to the load, C is the known capacitance of the capacitor, $V_i$ is the measured pre-discharge voltage on the capacitor at the time the capacitor is connected from the load, $V_f$ is the measured post-discharge voltage on the capacitor at the time the capacitor is disconnected from the load, and R is the purely resistive impedance of the load into which the capacitor is discharging.

Step 50 shows the use of the recalled circuit model, the beginning measured voltage, and the ending measured voltage, along with the measured time during which the capacitor discharged in order to solve for the electrical resistance of the biological tissues 20 through which the capacitor discharged. That is, with C being known and with $V_i$ and $V_f$ and t having been measured, R can be solved for, and this is how the method determines the electrical resistance of the biological tissues. It must be noted that this calculated electrical resistance will only be completely accurate if one capacitor (which may be composed of multiple capacitive elements) discharges through a single path. Multiple capacitors discharging through multiple paths will not yield completely accurate impedance measurements. However, even though the impedance calculation will not be completely accurate for multiple capacitors discharging through multiple paths, the energy discharge calculation, discussed below, will still be valid in such a situation. Hence, the multiple capacitor-multiple path impedance measurements will still be useful.

Step 52 depicts using the measured pre-discharge and post-discharge voltage on the capacitor in order to measure the energy discharged into the load; specifically, in one embodiment of the present invention, the capacitor energy equation of $CV^2/2$, where C is the known capacitance of the capacitor, and V is the voltage on the capacitor at some time, is used with the measured pre-discharge initial voltage on the capacitor to calculate the beginning pre-discharge energy stored in the capacitor; the same equation is also used with the measured post-discharge final voltage on the capacitor calculate the ending post-discharge energy stored in the capacitor. The difference in the pre-discharge and post-discharge energies is then designated the energy delivered to the biological tissues 20 during discharge.

Method step 56 illustrates the end step of the method wherein the energy discharged and the electrical resistance are determined.

While the invention has been particularly shown and described with reference to a preferred embodiment, it will be understood by those skilled in the art that various changes in form and detail may be made therein without departing from the spirit and scope of the invention.

What is claimed is:

1. A method for determining the energy delivered from a capacitor to biological tissues by a defibrillator, and said method comprising the steps of:

indicating that said capacitor is in the process of being connected to a load;

measuring a pre-discharge voltage across said capacitor to be discharged into biological tissues in response to an indication that said capacitor is in the process of being connected to said load;

indicating that said capacitor has been disconnected from said load;

measuring a post-discharge voltage across said capacitor which has been discharged into said biological tissues in response to an indication that said capacitor has been disconnected from said load; and calculating the energy delivered to said biological tissues based upon said measured pre-discharge and post-discharge voltages.

2. The method of claim 1, wherein said step of calculating further comprises the steps of:

using said measured pre-discharge voltage to calculate a beginning energy in said capacitor;

using said measured post-discharge voltage to calculate an ending energy in said capacitor; and calculating a difference between said beginning and ending energies in said capacitor and designating such difference to be said energy delivered to said biological tissues during said discharge.

3. A defibrillator incorporating a device for determining the energy delivered from a capacitor to biological tissues, said device comprising:

means for indicating that a capacitor is in the process of being connected to a load;

means for measuring a pre-discharge voltage across said capacitor to be discharged into biological tissues in response to an indication that said capacitor is in the process of being connected to said load;

means for indicating that said capacitor has been disconnected from said load;

means for measuring a post-discharge voltage across said capacitor which has been discharged into said biological tissues in response to an indication that said capacitor has been disconnected from said load; and means for calculating the energy delivered to said biological tissues based upon said measured pre-discharge and post-discharge voltages.

4. The device of claim 3, wherein said means for calculating further comprises:

means for using said measured pre-discharge voltage to calculate a beginning energy in the capacitor;

means for using said measured post-discharge voltage to calculate an ending energy in the capacitor; and means for calculating a difference between said beginning and ending energies and designating such difference to be the energy delivered to said biological tissues during said discharge.

* * * * *